(12) United States Patent
Kawata

(10) Patent No.: US 9,273,331 B2
(45) Date of Patent: Mar. 1, 2016

(54) PROCESS FOR PRODUCING 3-HYDROXYBUTYRIC ACID OR SALT THEREOF

(71) Applicant: National Institute of Advanced Industrial Science and Technology, Tokyo (JP)

(72) Inventor: Yoshikazu Kawata, Ikeda (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 21 days.

(21) Appl. No.: 14/345,591

(22) PCT Filed: Oct. 1, 2012

(86) PCT No.: PCT/JP2012/075352
§ 371 (c)(1),
(2) Date: Mar. 18, 2014

(87) PCT Pub. No.: WO2013/051499
PCT Pub. Date: Apr. 11, 2013

(65) Prior Publication Data
US 2014/0363863 A1 Dec. 11, 2014

(30) Foreign Application Priority Data
Oct. 7, 2011 (JP) ................................. 2011-222685

(51) Int. Cl.
C12P 7/42 (2006.01)
C12P 7/52 (2006.01)

(52) U.S. Cl.
CPC .... *C12P 7/42* (2013.01); *C12P 7/52* (2013.01)

(58) Field of Classification Search
None
See application file for complete search history.

(56) References Cited

U.S. PATENT DOCUMENTS

| | | | |
|---|---|---|---|
| 5,461,073 A | 10/1995 | Katayama | |
| 2011/0104767 A1 | 5/2011 | Kawata et al. | |

FOREIGN PATENT DOCUMENTS

| | | | | |
|---|---|---|---|---|
| CH | 621148 | * | 1/1981 | ............. C12N 15/00 |
| DE | 10 2008 045237 A1 | | 3/2010 | |
| EP | 2202316 | * | 6/2010 | ............... C12N 1/20 |
| JP | H07-061924 A | | 3/1995 | |
| JP | 2010-168595 A | | 8/2010 | |
| JP | 2010-273582 A | | 12/2010 | |
| JP | 2011-050337 A | | 3/2011 | |
| JP | 2011-083204 A | | 4/2011 | |
| WO | WO 2009/041531 A | | 4/2009 | |

OTHER PUBLICATIONS

Quillaguaman et al., Poly (3-hydroxybutyrate) production by a moderate halophile, Halomonas boliviensis LC1 using starch hydrolysate as substrate. Journal of Applied Microbiology, 2005, vol. 99, pp. 151-157.*
Machine translation of CH621148, provided by Scientific and Technical Information Center-Translations, Dec. 9, 2015.*
Kato et al., *Annual Report of Public Health and Environment Research Division of Mie Prefectural Science and Technology Promotion Center*, 9(52): 27-32 (2007).
Kawata et al., *Biosci. Biotechnol. and Biochem.*, 74(1): 175-177 (2010).
Kawata et al., *Journal of Bioscience and Bioengineering*, 113(4): 456-460 (2012).
Lee et al., *Biotechnology and Bioengineering*, 65(3): 363-368 (1999).
Liu et al., *Appln. Microbiol. Biotechnol.*, 76: 811-818 (2007).
Monteil-Rivera et al., *Journal of Chromatography A*, 1154: 34-41 (2007).
Research Institute of Innovative Technology for the Earth (RITE), 15th Report on Survey of Trends in Innovative Earth Technology (Jan. 31, 2006).
Ugwu et al., *Bioresource Technology*, 102(12): 6766-6768 (2011).
Japanese Patent Office, International Search Report in International Patent Application No. PCT/JP2012/075352 (Nov. 13, 2012).
Burgess et al., *Journal of Biotechnology*, 162: 57-66 (2012).
Kawata et al., *Appl. Microbiol. Biotechnol.*, 96: 913-920 (2012).
Matsumoto et al., *Appl. Microbiol. Biotechnol.*, 97:205-210 (2013).
National Institute of Advanced Industrial Science and Technology, "Production of 3-hydroxybutyric acid by *Halomonas* sp. KM-1 using surplus biomass," New Technology Presentation Meetings on Feb. 24, 2012, pp. 1-2 [retrieved from internet at URL: http://www.jstshingi.jp/aist/2011/pamphlet.pdf] (2011).
Nikel et al., *Appl. Microbiol. Biotechnol.*, 77: 1337-1343 (2008).
European Patent Office, Supplementary European Search Report in European Patent Application No. 12837739 (Mar. 6, 2015).

* cited by examiner

*Primary Examiner* — Thane Underdahl
*Assistant Examiner* — Yvonne Pyla
(74) *Attorney, Agent, or Firm* — Leydig, Voit & Mayer, Ltd.

(57) ABSTRACT

The invention provides a process for producing 3-hydroxybutyric acid or a salt thereof. The process includes (1) culturing one or more halophilic bacteria belonging to the genus *Halomonas* under aerobic conditions in a medium containing an inorganic salt and one or more organic carbon sources; (2) changing the culture conditions from aerobic culture to microaerobic culture, and culturing bacterial cells of the halophilic bacteria to produce 3-hydroxybutyric acid or a salt thereof in a culture medium; and (3) collecting the 3-hydroxybutyric acid or the salt thereof from the culture medium.

8 Claims, 5 Drawing Sheets

SEQUENCE LISTING

<160> NUMBER OF SEQ ID NOS: 2

<210> SEQ ID NO 1
<211> LENGTH: 19

-continued

```
<212> TYPE: DNA
<213> ORGANISM: Artificial Sequence
<220> FEATURE:
<223> OTHER INFORMATION: Primer

<400> SEQUENCE: 1
tgggtccttc gcggactttt                                          19

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
cgtctccgaa gggttcgcag g                                        21
```

PROCESS FOR PRODUCING 3-HYDROXYBUTYRIC ACID OR SALT THEREOF

CROSS-REFERENCE TO RELATED APPLICATIONS

This patent application is the U.S. national phase of International Patent Application No. PCT/JP2012/075352, filed Oct. 1, 2012, which claims the benefit of Japanese Patent Application No. 2011-222685, filed on Oct. 7, 2011, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 707 bytes ASCII (Text) file named "716377SequenceListing.txt," created Mar. 17, 2014.

TECHNICAL FIELD

The present invention relates to a process for producing 3-hydroxybutyric acid or a salt thereof.

BACKGROUND ART

Amid recent concerns about peak oil, urgent issues have arisen, such as the shift to bio-based technologies for not only energy but also chemical refineries, and it became a critical issue that the conversion of industrial starting materials from petroleum to biomass.

In humans, 3-hydroxybutyric acid, which is produced from acetyl CoA in the liver, is used as an energy source for the brain when blood glucose levels are low. Further, it can prevent the transfer of enterobacteria into the blood (PTL 1). Therefore, 3-hydroxybutyric acid is used in infusions. This compound is also used as a starting material for biodegradable plastics.

Referring to the "Hopeful 32 Starting Materials for Biorefineries" shown in NPL 1, 3-hydroxybutyric acid is mentioned as a promising compound as a starting or intermediate material for biorefineries. Further expanded use of this compound is highly expected.

Known processes for producing 3-hydroxybutyric acid are as follows. For example, since this compound is a monomer of poly-3-hydroxybutyrate (hereinafter also referred to as "PHB" in the present specification), PHB is produced by various bacterial cells, and then degraded by lipases, etc., which have been prepared separately, to thereby obtain 3-hydroxybutyric acid, which is a monomer of PHB (PTL 2). NPL 2 shows a process in which 8.7 g/L of 3-hydroxybutyric acid is obtained by using mutants, and NPL 3 shows a process in which 3-hydroxybutyric acid is obtained with a yield of 12 g/L by using a gene recombination technique.

The present inventor examined an efficient process of culturing Spirulina microalgae, which is known to have little contamination by other bacteria during commercial outdoor incubation, and found that specific halophilic bacterium, grew under certain conditions as the only contaminating bacterium. Since in general the halophilic bacteria generally grew well in a medium with a pH of about 5 to 12 containing a high concentration of sodium, it was presumed that contamination by other bacteria hardly occurred, even under aerobic fermentation. Then, examination of the assimilation of various carbon sources by the halophilic bacteria revealed that a remarkable amount of polyhydroxyalkanoates (PHAs) was accumulated in the cells of the halophilic bacteria (PTL 3).

Moreover, PTL 4 shows studies specific to the production of PHAs by the halophilic bacteria, and the halophilic bacteria are known to be involved in the production of specific substances, such as lactic acid and acetic acid (PTL 4). Furthermore, NPL 6 reports a process for producing 3-hydroxybutyric acid with a yield of 117 g/L by culturing bacterial cells belonging to a specific genus, and then subjecting the bacterial cells to autolysis under anaerobic conditions for about 6 hours.

CITATION LIST

Patent Literature

PTL 1: JP7-61924A
PTL 2: JP2010-168595A
PTL 3: WO2009/041531
PTL 4: JP2010-273582A

Non-Patent Literature

NPL 1: 15th Report on Survey of Trends in Innovative Earth Technology, "Demand for Sustainable Development: Early Construction of Biorefinery Industry," Hideaki Yukawa, Microbiology Research Group, Research Institute of Innovative Technology for the Earth (RITE), Jan. 31, 2006
NPL 2: Bioresource Technology, Volume 102, Issue 12, June 2011, pp. 6766-6768, Charles U. Ugwu, Yutaka Tokiwa, and Toshio Ichiba
NPL 3: Appl Microbiol Biotechnol (2007) 76:811-818 Qian Liu, Shao-Ping Ouyang, Ahleum Chung, Qiong Wu, and Guo-Qiang Chen
NPL 4: Annual Report of Public Health and Environment Research Division of Mie Prefectural Science and Technology Promotion Center, No. 9 (Serial Volume No. 52), pp. 27-32, 2007
NPL 5: J. Chromatogr. A, Jun. 22, 2007; 1154(1-2):34-41, Monteil-Rivera F et al.
NPL 6: Biotechnol. Bioeng. 65, 363-368, (1999) Lee, S. Y., Lee, Y., Wang, F.

SUMMARY OF INVENTION

Technical Problem

A primary object of the present invention is to provide an inexpensive, simple, and highly efficient process for producing 3-hydroxybutyric acid or a salt thereof. NPL 6, mentioned above, discloses a process for producing 3-hydroxybutyric acid using bacterial cells. Bacterial cells of *Alcaligenes latus* are used, and 3-hydroxybutyric acid is produced while lysing the bacterial cells. Accordingly, the process has the following problems: it is necessary to be careful about contamination by other bacterial cells during the culture of the above cells, expensive media are required, and it is necessary to purify 3-hydroxybutyric acid from the lysate containing many impurities, such as DNA and protein, which are derived from the bacterial cells.

The present inventor found that when halophilic bacteria belonging to a specific genus were cultured using a medium containing an inorganic salt and one or more organic carbon sources, the bacteria accumulated PHB in their cells (PTL 3).

Since PHB was accumulated in the bacterial cells as an energy source or a carbon source, it was assumed that when carbon sources were exhausted, thereby causing lack of energy, PHB in the cells was degraded and used through glycolysis and TCA cycle under aerobic conditions. However, there are no reports on how this works under microaerobic or anaerobic conditions.

Solution to Problem

The present inventor conducted extensive research against this background and found that when halophilic bacteria belonging to a specific genus were cultured under aerobic conditions to cause the bacteria to accumulate PHB in their cells, and the culture conditions were then changed to microaerobic conditions, PHB in the bacterial cells was degraded and reduced, and 3-hydroxybutyric acid or a salt thereof was produced in the medium outside of the bacterial cells.

It was also found that, for PHB accumulation, the bacteria could be cultured using biodiesel (hereinafter also referred to as BDF (registered trademark) in the present specification) waste water etc., co-cultured with Spirulina, which is photosynthetic microalgae, and cultured in an environment where contamination by other bacteria hardly occurred.

It was further revealed that since the production of 3-hydroxybutyric acid or a salt thereof from PHB was performed with a sequence of growth of halophilic bacterial cells belonging to a specific genus, 3-hydroxybutyric acid or a salt thereof could be produced by using the same culture tank and changing only the culture conditions, without changing the medium.

The present invention has been accomplished upon further studies based on these findings, and widely includes a process for producing 3-hydroxybutyric acid or a salt thereof shown below.

Item 1
A process for producing 3-hydroxybutyric acid or a salt thereof, the process comprising the following steps (1) to (3):
  (1) step 1 of culturing one or more halophilic bacteria belonging to the genus *Halomonas* under aerobic conditions in a medium containing an inorganic salt and one or more organic carbon sources;
  (2) step 2 of changing the culture conditions in step 1 from aerobic culture to microaerobic culture, and culturing bacterial cells of the halophilic bacteria to produce 3-hydroxybutyric acid or a salt thereof in a culture medium; and
  (3) step 3 of collecting the 3-hydroxybutyric acid or the salt thereof from the culture medium obtained in step 2.

Item 2
The process according to Item 1, wherein the 3-hydroxybutyric acid or the salt thereof is contained in an amount of 3 g or more per liter of the culture medium obtained in step 2.

Item 3
The process according to Item 1 or 2, wherein the organic carbon sources comprise glycerol or waste glycerol.

Item 4
The process according to any one of Items 1 to 3, wherein the halophilic bacteria comprise *Halomonas* sp. KM-1 strain (FERM BP-10995).

Advantageous Effects of Invention

The effects of the production process of the present invention are described below; however, the production process of the present invention does not necessarily exhibit all the following effects, but may have one or more of those effects.

According to the production process of the present invention, a remarkable amount of 3-hydroxybutyric acid or a salt thereof can be accumulated in the medium, and a part of the same can be accumulated in the bacterial cells.

The production process of the present invention includes the step of culturing halophilic bacteria belonging to the genus *Halomonas*. The halophilic bacteria can be cultured in an environment where contamination by other bacteria hardly occurs, and the air supply conditions can be easily changed. Therefore, the production process of the present invention is excellent.

The halophilic bacteria used in the production process of the present invention can use, for example, inexpensive inorganic salts, as well as waste glycerol produced as a by-product in the production of biodiesel, wood saccharification liquid produced in the process of ethanol fermentation, etc., as organic carbon sources singly or in combination with other organic carbon sources. Further, pentoses, such as xylose and arabinose, which are obtained by ethanol fermentation using yeast cells and are difficult to use, can also be effectively used as organic carbon sources.

This suggests the possibility of producing 3-hydroxybutyric acid or a salt thereof by using, as an organic carbon source, for example, a residue after ethanol fermentation of wood saccharification liquid (mainly containing xylose and arabinose) by means of existing yeast cells that do not undergo genetic recombination.

The production process of the present invention can produce 3-hydroxybutyric acid or a salt thereof in the medium. Fractions containing the 3-hydroxybutyric acid or the salt thereof can be easily collected from the culture medium. Even when purification is performed, a simple purification method can be applied. Therefore, the production process of the present invention is excellent.

In this regard, because the 3-hydroxybutyric acid or the salt thereof can be collected from the culture medium of the halophilic bacterial cells belonging to the genus *Halomonas* under conditions that do not cause bacteriolysis of the cells, the production process of the present invention has the effect of purifying the 3-hydroxybutyric acid or the salt thereof by a very simple purification method for removing contaminating molecules, such as nucleic acid, protein, sugar, and lipid, resulting from bacteriolysis.

The 3-hydroxybutyric acid or the salt thereof obtained by the production process of the present invention can be added to medical infusions, or polymerized as it is to form a plastic material. The 3-hydroxybutyric acid or the salt thereof is also useful as an optically active starting material for cosmetics, drugs, functional foods, etc., and useful in refineries.

Figure 2:
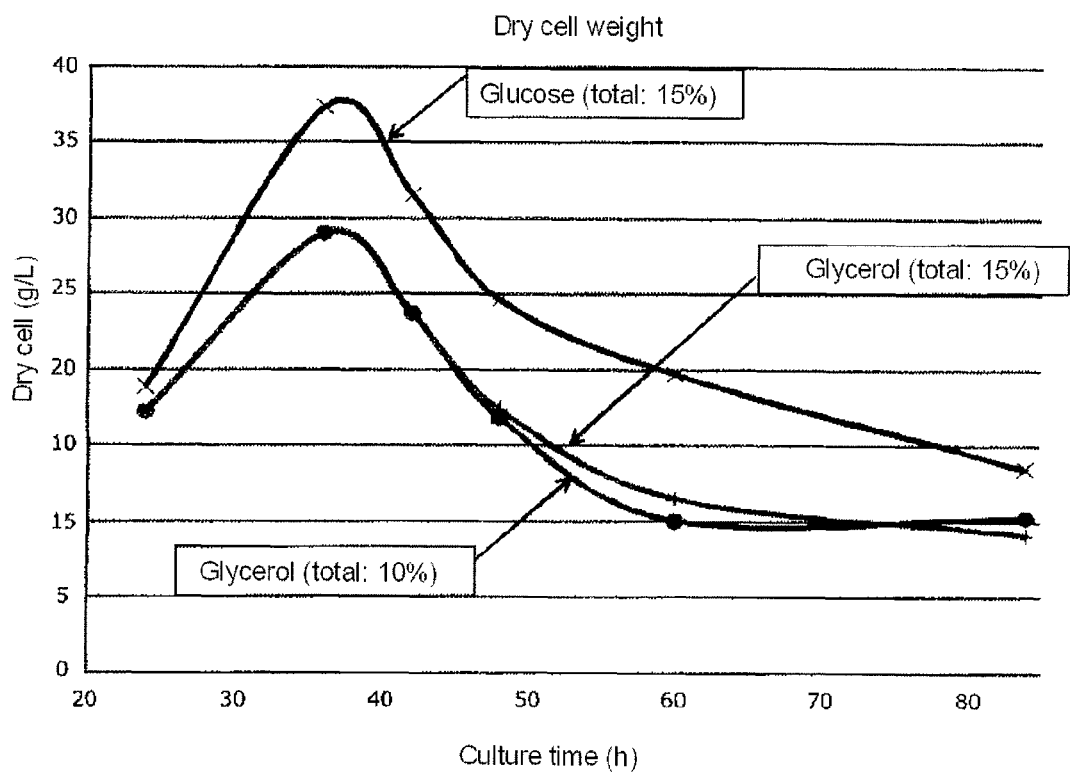

FIG. 2 is a graph showing the accumulated dry cell weight (vertical axis: g/L) and the culture time (horizontal axis: h) when halophilic bacterium *Halomonas* sp. KM-1 strain was cultured at 33° C. using glucose or glycerol.

Figure 3:
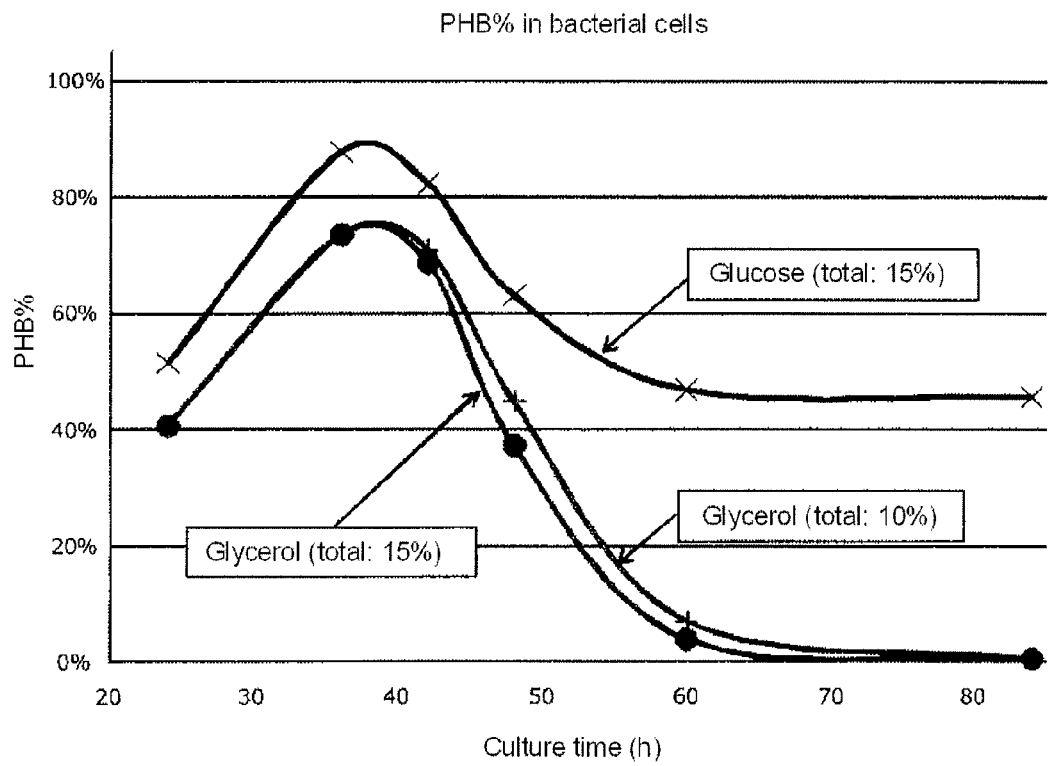

FIG. 3 is a graph showing the PHB accumulation rate (vertical axis: PHB/dry cell (%)) and the culture time (horizontal axis: h) when halophilic bacterium *Halomonas* sp. KM-1 strain was cultured at 33° C. using glucose or glycerol.

Figure 4:
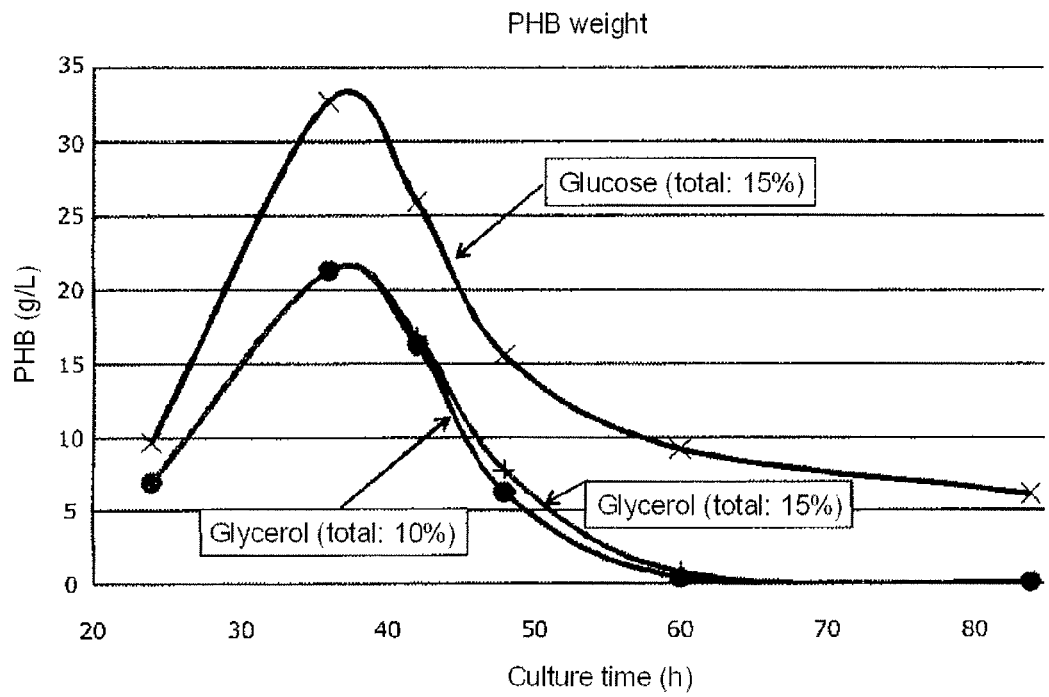

FIG. 4 is a graph showing the total amount of PHB accumulated (vertical axis: g (PHB)/L (culture medium)) and the culture time (horizontal axis: h) when halophilic bacterium *Halomonas* sp. KM-1 strain was cultured at 33° C. using glucose or glycerol.

Figure 5:
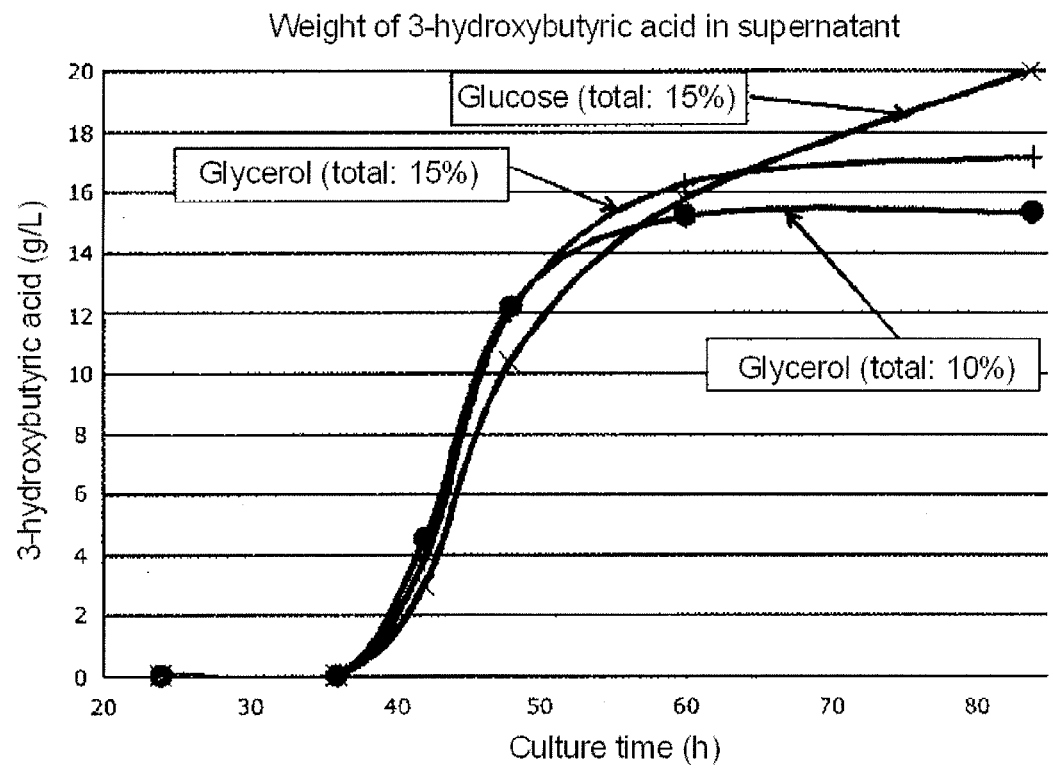

FIG. 5 is a graph showing the accumulation rate of 3-hydroxybutyric acid or a salt thereof in the supernatant (vertical axis: 3-hydroxybutyric acid or salt thereof (g)/culture supernatant (L)) and the culture time (horizontal axis: h) when halophilic bacterium *Halomonas* sp. KM-1 strain was cultured at 33° C. using glucose or glycerol.

Figure 6:
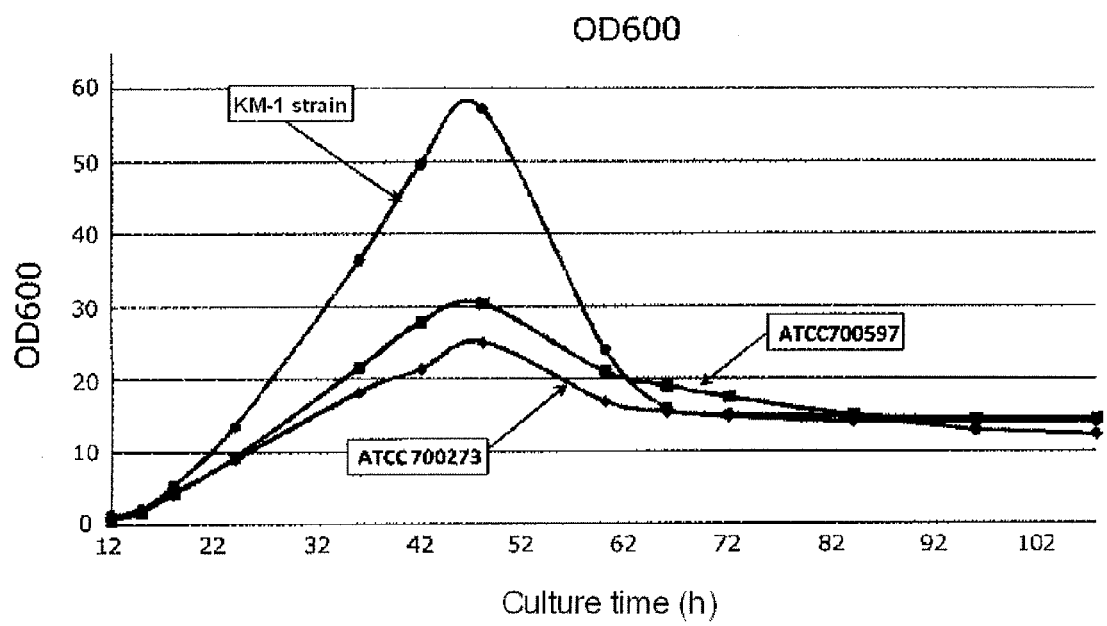

FIG. 6 is a graph showing the culture turbidity OD600 (vertical axis) and the culture time (horizontal axis: h) when halophilic bacteria *Halomonas* sp. KM-1 strain, *Halomonas pantelleriensis* (ATCC 700273), and *Halomonas campisalis* (ATCC 700597) were cultured at 33° C. using 10% glycerol. The symbol "%" shown in the legend represents "w/v %" At the beginning of culture, the strains were cultured under aerobic conditions at 200 rpm. At the 48th hour, the conditions were changed to microaerobic conditions at 50 rpm. The following conditions are such that analytical values when the same culture was performed are shown in graphs.

Figure 7:
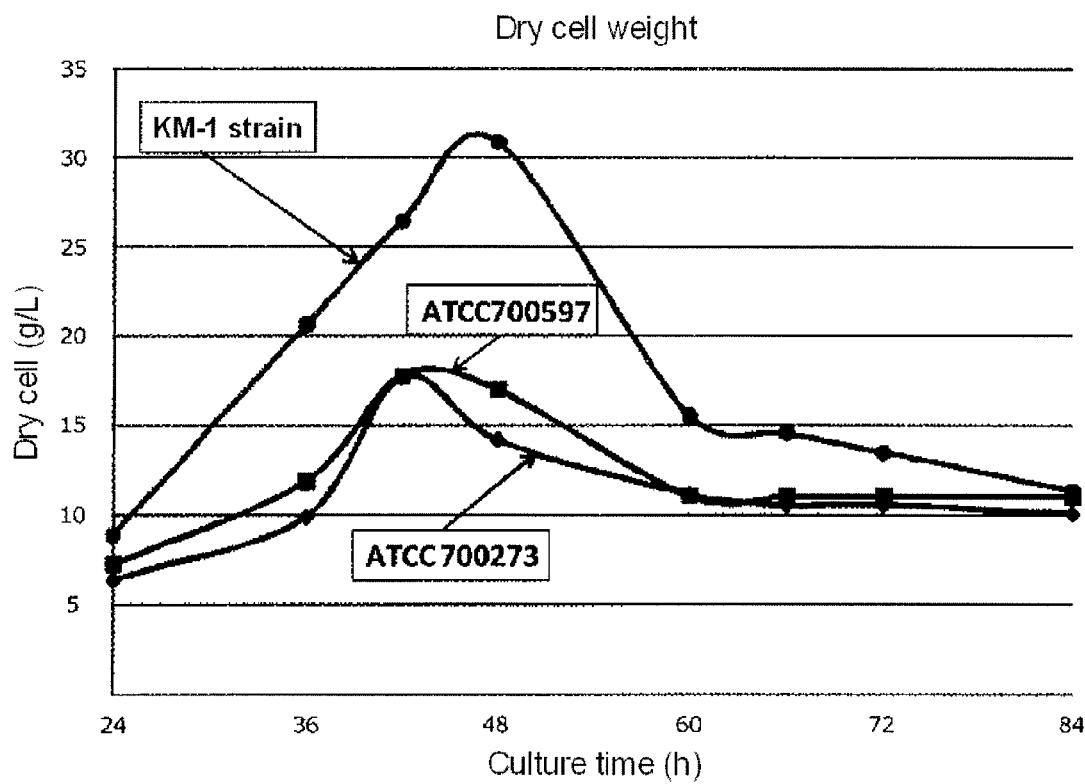

FIG. 7 is a graph showing the accumulated dry cell weight (vertical axis: g/L) and the culture time (horizontal axis: h) when halophilic bacteria *Halomonas* sp. KM-1 strain, *Halomonas pantelleriensis* (ATCC 700273), and *Halomonas campisalis* (ATCC 700597) were cultured at 33° C. using 10% glycerol.

Figure 8:
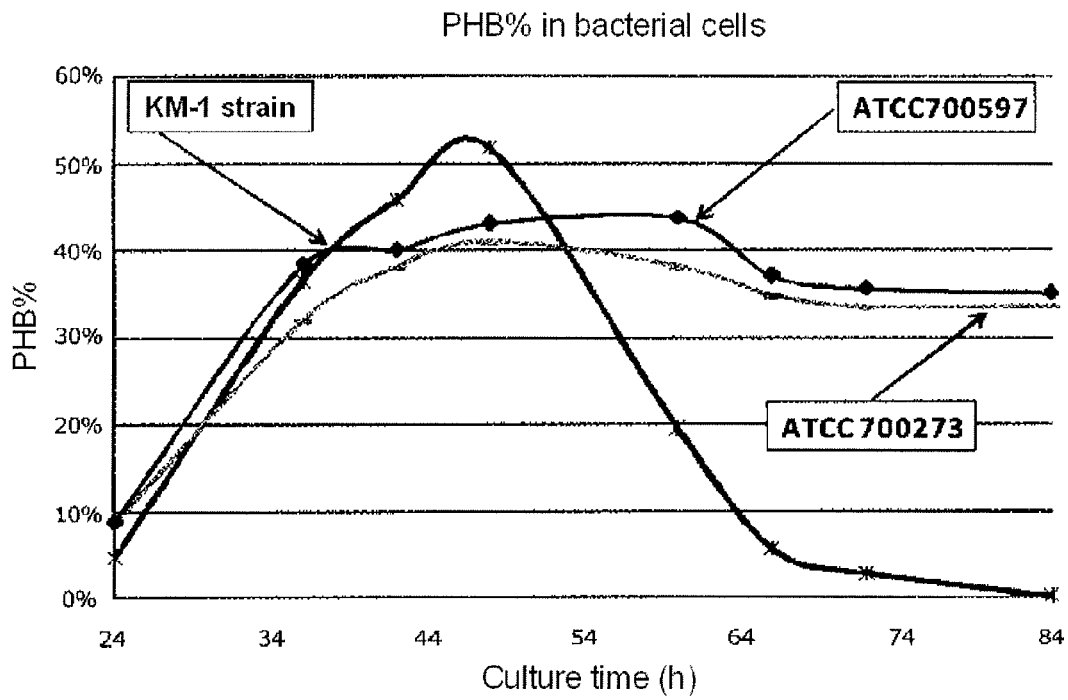

FIG. 8 is a graph showing the PHB accumulation rate (vertical axis: PHB/dry cell (%)) and the culture time (horizontal axis: h) when halophilic bacteria *Halomonas* sp. KM-1 strain, *Halomonas pantelleriensis* (ATCC 700273), and *Halomonas campisalis* (ATCC 700597) were cultured at 33° C. using 10% glycerol.

Figure 9:
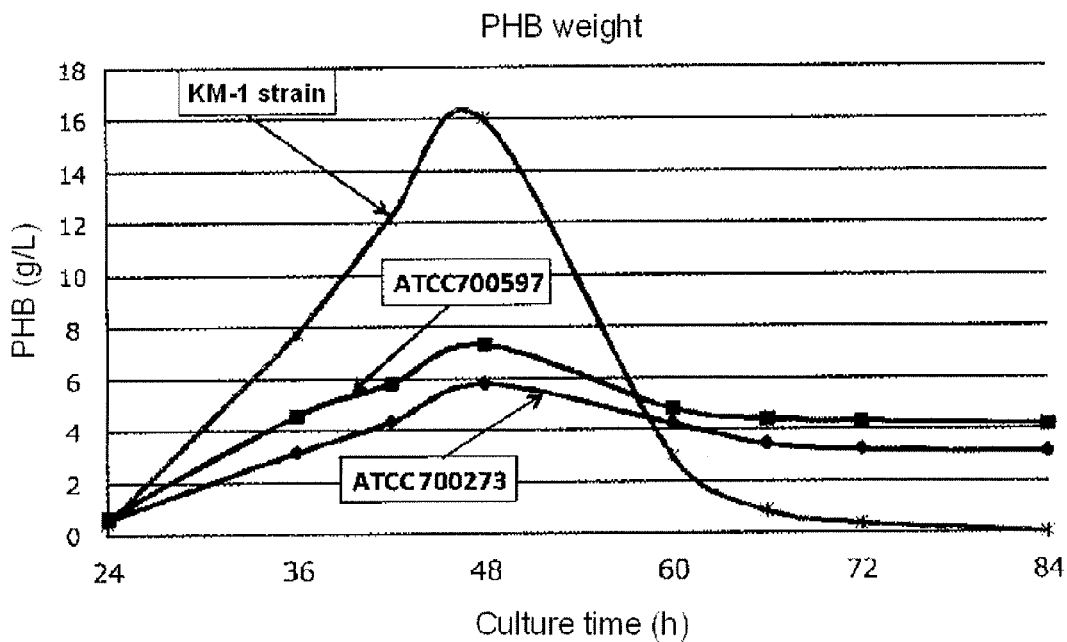

FIG. 9 is a graph showing the total amount of PHB accumulated (vertical axis: g (PHB)/L (culture medium)) and the culture time (horizontal axis: h) when halophilic bacteria *Halomonas* sp. KM-1 strain, *Halomonas pantelleriensis* (ATCC 700273), and *Halomonas campisalis* (ATCC 700597) were cultured at 33° C. using 10% glycerol.

Figure 10:
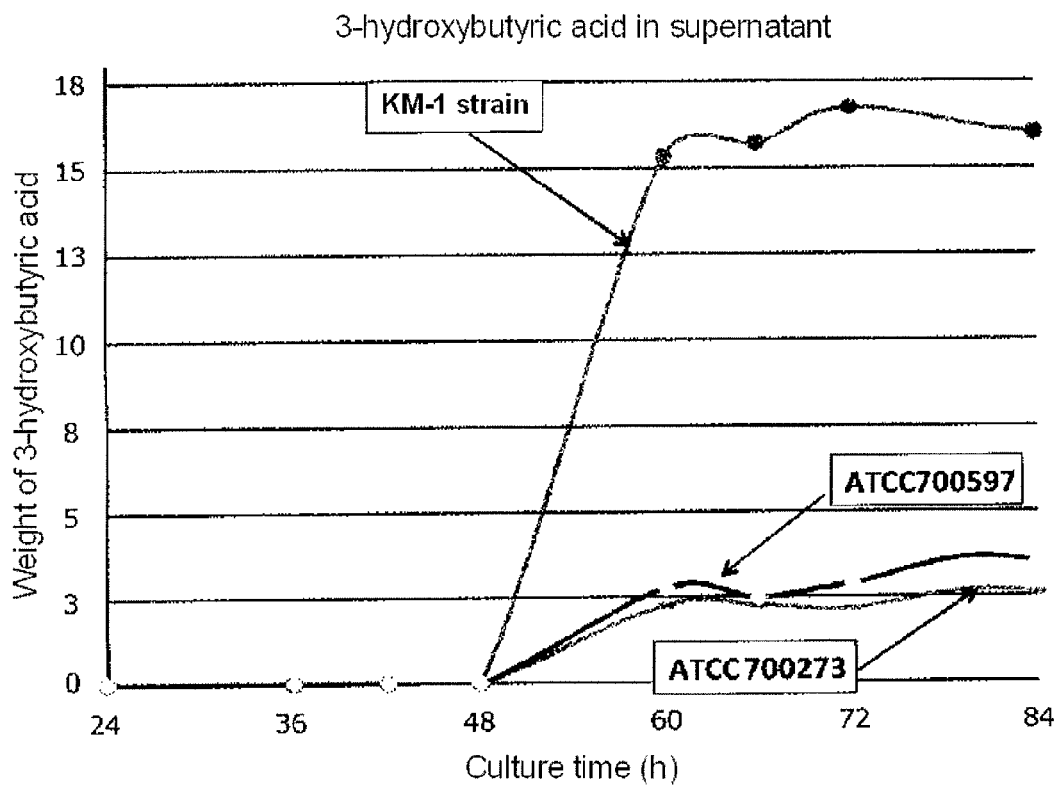

FIG. 10 is a graph showing the accumulation rate of 3-hydroxybutyric acid or a salt thereof in the supernatant (vertical axis: 3-hydroxybutyric acid (g)/culture supernatant (L)) and the culture time (horizontal axis: h) when halophilic bacteria *Halomonas* sp. KM-1 strain, *Halomonas pantelleriensis* (ATCC 700273), and *Halomonas campisalis* (ATCC 700597) were cultured at 33° C. using 10% glycerol.

DESCRIPTION OF EMBODIMENTS

The process for producing 3-hydroxybutyric acid or a salt thereof according to the present invention uses halophilic bacteria belonging to the genus *Halomonas* and comprises the following steps (1) to (3):
(1) step 1 of culturing one or more halophilic bacteria belonging to the genus *Halomonas* under aerobic conditions in a medium containing an inorganic salt and one or more organic carbon sources;
(2) step 2 of changing the culture conditions in step 1 from aerobic culture to microaerobic culture, and culturing bacterial cells of the halophilic bacteria to produce 3-hydroxybutyric acid or a salt thereof in a culture medium; and
(3) step 3 of collecting the 3-hydroxybutyric acid or the salt thereof from the culture medium obtained in step 2.

The 3-hydroxybutyric acid or the salt thereof produced by the production process of the present invention is a compound having ordinary optical activity in the living body, and is D-isomer.

Salts of 3-hydroxybutyric acid are formed by cations derived from components contained in the medium of the halophilic bacteria belonging to the genus *Halomonas* used in the production. Examples thereof include sodium salts, potassium salts, calcium salts, magnesium salts, cobalt salts, zinc salts, iron salts, copper salts, and the like.

Step 1

Step 1 of the process for producing 3-hydroxybutyric acid or a salt thereof according to the present invention is a step of culturing halophilic bacteria belonging to the genus *Halomonas* under aerobic conditions in a medium containing an inorganic salt and one or more organic carbon sources.

A: Halophilic Bacteria

The halophilic bacteria used in step 1 of the production process of the present invention may be those belonging to the genus *Halomonas* shown in (i) or (ii) below:
(i) Halophilic bacteria that grow aerobically in a medium containing an inorganic salt and one or more organic carbon sources, and that produce 3-hydroxybutyric acid or a salt thereof in a medium outside of the bacterial cells; or
(ii) Halophilic bacteria that grow aerobically in a medium containing an inorganic salt and one or more organic carbon sources, and that accumulate PHB in their own bacterial cells and then produce 3-hydroxybutyric acid or a salt thereof in a culture medium outside of the bacterial cells under microaerobic conditions.

The inorganic salt and organic carbon sources will be described later in the column of "Medium" section. The microaerobic conditions will be described in detail below in the "Culture Method" section in step 2.

Such halophilic bacteria belonging to the genus *Halomonas* can undergo both oxidative metabolism and anaerobic metabolism, and can survive regardless of the presence of free oxygen. They also have the properties of the "facultative anaerobes," which tend to grow better in the presence of free oxygen.

The halophilic bacteria belonging to the genus *Halomonas* have halophilic properties that prefer a salt concentration of 0.1 to 1.0 M, and they can occasionally grow in a salt-free medium. The halophilic bacteria belonging to the genus *Halomonas* generally grow in a medium with a pH of about 5 to 12.

The halophilic bacteria belonging to the genus *Halomonas* are, for example, *Halomonas* sp. KM-1 strain. The *Halomonas* sp. KM-1 strain was deposited with the National Institute of Advanced Industrial Science and Technology International Patent Organism Depositary (Chuo-6, Higashi 1-1-1, Tsukuba-shi, Ibaraki, 305-8566, Japan) under the accession number FERM P-21316 dated Jul. 10, 2007, and has been internationally deposited under the accession number FERM BP-10995. The 16S rRNA gene of *Halomonas* sp. KM-1 strain has been registered in DDBJ under the accession number AB477015.

Moreover, in view of the above growth characteristics of the halophilic bacteria belonging to the genus *Halomonas*, *Halomonas pantelleriensis* (ATCC 700273), *Halomonas campisalis* (ATCC 700597), and other halophilic bacteria can also be used in the production process of the present invention, in addition to the *Halomonas* sp. KM-1 strain.

Furthermore, 16S ribosomal RNA sequence analysis shows that not only can the above halophilic bacteria belonging to the genus *Halomonas*, but also *Halomonas nitritophilus*, *Halomonas alimentaria*, etc., be used as the halophilic bacteria belonging to the genus *Halomonas* used in the production process of the present invention.

Genes may be introduced into the halophilic bacteria belonging to the genus *Halomonas*. Genes to be introduced are not particularly limited, as long as they can develop the function of improving the production efficiency, etc., of 3-hydroxybutyric acid or a salt thereof in the production process of the present invention. Examples thereof include genes that increase PHB expression levels, genes that develop the function of increasing PHB accumulation in the bacterial cells, genes that promote the function of producing 3-hydroxybutyric acid or a salt thereof in the culture medium, genes that increase the amount of 3-hydroxybutyric acid or a salt thereof produced, genes that degrade PHB, and the like.

The introduction of such genes into the halophilic bacteria belonging to the genus *Halomonas* is carried out in the following manner. Recombinant DNA that allows expression of the introduced genes in the bacterial cells is produced and introduced into the bacterial cells for transformation. For example, it is preferable to use an expression plasmid obtained by using a plasmid vector replicable in the bacterial cells, and locating a promoter, SD (Shine and Dalgarno) base sequence, and initiation codon (e.g., ATG) necessary for the initiation of transcription, upstream of the gene so that the gene can be expressed in this vector. As the method of introducing the desired recombinant DNA obtained in this way to the bacterial cells, and the method of transformation with the recombinant DNA, various general methods can be used.

B: Medium

The medium used in step 1 contains an inorganic salt and one or more organic carbon sources. Although the pH of the medium is not particularly limited, the pH preferably satisfies the above growth conditions of the halophilic bacteria. Specifically, the pH is preferably about 5 to 12, and more preferably 8.8 to 12. The use of an alkaline medium is preferred because contamination by other bacteria can be prevented more effectively.

The inorganic salt added to the medium used in step 1 is not particularly limited. Examples thereof include phosphate, nitrate, carbonate, and sulfate; and metal salts of sodium, magnesium, potassium, manganese, iron, zinc, copper, cobalt, etc.

For example, when sodium is used as the inorganic salt, it is possible to use NaCl, $NaNO_3$, $NaHCO_3$, $Na_2CO_3$, or the like.

As these inorganic salts, it is preferable to use compounds that can serve as nitrogen sources or phosphorus sources for the halophilic bacteria.

Examples of nitrogen sources include nitrate, nitrite, ammonium salts, etc. Specific examples include $NaNO_3$, $NaNO_2$, $NH_4Cl$, and other compounds.

The amount of nitrogen source used may be suitably determined within a range that does not affect the growth of the bacterial cells and that can achieve the purpose of the present invention to produce 3-hydroxybutyric acid or a salt thereof. Specifically, the amount as nitrate salts per 100 ml of the medium is generally about 500 mg or more, preferably about 1,000 mg or more, and more preferably about 1,250 mg or more.

Moreover, examples of phosphorus sources include phosphate, monohydrogen phosphate, dihydrogen phosphate, etc. Specific examples include $K_2HPO_4$, $KH_2PO_4$, and other compounds.

The amount of phosphorus source used may also be suitably determined from the same viewpoint as for the amount of nitrogen source mentioned above. More specifically, the amount of dihydrogen phosphate per 100 ml of the medium is generally about 50 to 400 mg, and preferably about 100 to 200 mg.

These inorganic salts may be used singly or in combination of two or more.

The total concentration of inorganic salt, including other compounds, etc., is generally about 0.1 to 2.5 M, preferably about 0.2 to 1.0 M, and more preferably about 0.2 to 0.5 M.

The organic carbon source added to the medium used in step 1 is not particularly limited. Examples thereof include tryptone, yeast extract, soluble starch, hexoses (glucose, fructose), pentoses (xylose, arabinose), disaccharide (sucrose), sugar alcohols (mannitol, sorbitol), ethanol, n-propanol, acetic acid, sodium acetate, propionic acid, glycerol, waste glycerol, and the like.

In addition, exhausted molasses, wood saccharification liquid, or their residues can also be used as the organic carbon source. Among these, waste glycerol, exhausted molasses, etc., are preferred in terms of reducing the cost of the production process. These organic carbon sources may be used singly or in combination of two or more.

Waste glycerol usable in the present invention is produced as a by-product in the production of fatty acid methyl ester-based biodiesel, and obtained by adding an alcohol (e.g., methanol) and an alkaline catalyst (e.g., KOH or NaOH) to oils and fats derived from plants, animals, or the like, and reacting the mixture at a temperature of about 65° C.

The composition of the waste glycerol is not particularly limited, and varies depending on the production facilities for biodiesel and the composition of oils and fats used as starting materials. For example, as shown in NPL 4, waste glycerol with a glycerol concentration of about 30 to 65% can be used, which contains about 4 to 7% of an alkaline catalyst mentioned above, and has a pH of about 10 to 12. Moreover, the waste glycerol contains water that is used to wash the obtained biodiesel.

Although the amount of organic carbon source varies depending on the type of organic carbon source used, the final concentration of organic carbon source in the medium is generally about 1 to 20 w/v %.

In particular, when waste glycerol is used as an organic carbon source, the final concentration of waste glycerol in the medium is generally about 1 to 20 w/v %, and preferably about 10 to 15 w/v %.

According to the production process of the present invention, the halophilic bacteria belonging to the genus *Halomonas* are cultured in a medium with a relatively high salt concentration, and this causes little risk of contamination by other bacterial cells. Therefore, sterilization or other treatment is not required for the medium, and culture by using simple equipment is possible.

C: Culture Method

Aerobic culture is used to culture the halophilic bacteria belonging to the genus *Halomonas* in step 1. The aerobic culture in step 1 is not particularly limited, as long as it enables the bacterial cells to grow and to accumulate a large amount of PHB therein. For example, the halophilic bacteria are inoculated in about 5 ml of medium, and pre-cultured with shaking generally at about 30 to 37° C. and at a stirring rate of about 120 to 180 rpm overnight.

The pre-cultured cells are then diluted about 100 times in a medium that is placed in an Erlenmeyer flask, fermenter, jar fermenter, or the like, for main culture. The main culture is preferably carried out at about 30 to 37° C., although it is generally possible to carry out the main culture at 20 to 45° C. The stirring rate in this case is generally about 150 to 250 rpm. The culture environment may be such that the medium is exposed to the air. A gas containing oxygen may be actively sprayed to the surface of the culture medium, or the gas may be blown into the medium.

In step 1, the halophilic bacteria belonging to the genus *Halomonas* are aerobically cultured under such culture conditions. Specifically, the dissolved oxygen concentration of the culture medium during aerobic culture is generally 2 mg/L or more, but is not particularly limited thereto.

Examples of the culture method in step 1 include, but are not limited to, batch culture, fed-batch culture, continuous culture, and the like. Batch culture or fed-batch culture is preferred for efficient production of 3-hydroxybutyric acid or a salt thereof, in view of the very low risk of contamination of the halophilic bacteria used in the process of the present invention by other bacteria.

Step 2

Step 2 of the process for producing 3-hydroxybutyric acid or a salt thereof according to the present invention is a step of culturing the bacterial cells under microaerobic conditions after completion of step 1 to produce 3-hydroxybutyric acid or a salt thereof in a culture medium.

"Producing 3-hydroxybutyric acid in a culture medium" means that the halophilic bacteria belonging to the genus *Halomonas* obtained by culturing in step 1 secrete 3-hydroxybutyric acid into the culture medium from their cells. "Producing a salt of 3-hydroxybutyric acid in the culture medium" means that the 3-hydroxybutyric acid secreted into the culture medium is reacted with the above cationic components present in the culture medium to form a salt of 3-hydroxybutyric acid.

In step 2, it is only necessary to change the culture conditions to microaerobic conditions. After the halophilic bacteria belonging to the genus *Halomonas*, which accumulate PHB in their cells, obtained in step 1 are collected, they may be cultured in a new medium, cultured in the same medium while the culture conditions are changed to microaerobic conditions, or cultured with the addition of a new medium when step 1 is completed.

The time to end the aerobic culture in step 1 and change the culture conditions to microaerobic conditions in step 2 is preferably set to the time when the amount of PHB accumulated in the halophilic bacterial cells belonging to the genus *Halomonas* obtained in step 1 reaches the maximum value. The time of the maximum value is not necessarily limited to one time point; the culture conditions may be changed to microaerobic conditions when the amount of PHB accumulated in the bacterial cells is generally 60% or more of the maximum value. The amount of PHB in the bacterial cells can be measured by using the method shown in the Examples, described later.

D: Culture Method

The microaerobic culture in step 2 indicates culture without positive oxygen ventilation, rather than culture in a medium or culture environment under completely anaerobic conditions.

The culture method under such microaerobic conditions is not particularly limited. For example, the culture is carried out at a stirring rate of 100 rpm or less, preferably 50 rpm or less, while the medium surface is exposed to the air. It is not preferable to completely stop stirring in step 2, because dissolved oxygen in the culture medium will quickly disappear. The dissolved oxygen concentration of the culture medium is not particularly limited, but is generally 2 mg/L or less. In this case, conditions in which oxygen dissolved in the culture medium is completely absent are not preferable in step 2, because the halophilic bacteria belonging to the genus *Halomonas* immediately develop bacteriolysis.

In step 2, the halophilic bacteria belonging to the genus *Halomonas*, which accumulate a remarkable amount of PHB in their bacterial cells, obtained in step 1 are cultured under microaerobic conditions, thereby allowing the culture of the halophilic bacteria without extinction.

The extinction of the halophilic bacteria can be confirmed by the presence of DNA eluted from the bacterial cells into the culture medium resulting from the extinction of the bacterial cells. For example, the extinction can be confirmed by subjecting the culture supernatant of the halophilic bacteria to measurement by using a spectrophotometer to show that no significant absorbance peak based on DNA is present at around 260 nm.

Alternatively, the extinction can be confirmed by measuring the genomic DNA concentration of the supernatant using PCR primers (e.g., 832F: SEQ-ID-NO: 1; 1016R: SEQ ID NO: 2) specific to the 16S ribosomal RNA sequences of *Halomonas* bacteria (amplification length: 184 bp) and using a real-time PCR device.

The amount of DNA in the culture medium under the microaerobic conditions using the above method is generally about 0.5 to 2.5 mg/L during the period from the start of culture under microaerobic conditions to about 72 hours.

More specifically, in step 2, the halophilic bacteria belonging to the genus *Halomonas* may be cultured under conditions that cause the DNA amount in the culture medium to be within the above range. Such culture conditions that cause the above DNA amount in the culture medium provide one indication of the fulfillment of the microaerobic conditions in the present invention.

Although the culture time varies depending on the medium conditions, such as the inorganic salt, organic carbon source, etc., used in the medium, it may be a period of time sufficient for collecting the desired amount of 3-hydroxybutyric acid or a salt thereof, as described later, and is not particularly limited. The culture time may be suitably determined in consideration of simplifying the purification process to remove nucleic acid, protein, etc., released from the halophilic bacteria belonging to the genus *Halomonas* into the culture medium due to bacteriolysis, after the culture method is changed to microaerobic culture, as described above; that is, the DNA concentration of the culture medium, the concentration of 3-hydroxybutyric acid or salt thereof in the culture medium, and the like.

Step 3

Step 3 in the process for producing 3-hydroxybutyric acid or a salt thereof according to the present invention is a step of collecting the 3-hydroxybutyric acid or the salt thereof from the culture medium obtained in step 2. The term "collecting" as used herein means that after the culture in step 2 is stopped when 3-hydroxybutyric acid or a salt thereof is present in the culture medium obtained in step 2, the culture medium containing the 3-hydroxybutyric acid or the salt thereof is separated from the halophilic bacterial cells.

Specific separation techniques include known solid-liquid separation operations, such as centrifugation and filtration. Moreover, the method of stopping the culture is not particularly limited. For example, the halophilic bacteria are sterilized by heating, acid treatment, or the like; or the culture medium and the halophilic bacterial cells are separated by a known solid-liquid separation method, such as centrifugation or filtration, can be used.

When the culture is continued while the 3-hydroxybutyric acid or the salt thereof is contained in the culture medium, particularly under aerobic conditions, the halophilic bacteria reuptake and use the 3-hydroxybutyric acid or the salt thereof secreted into the culture medium. Consequently, the 3-hydroxybutyric acid or the salt thereof in the culture medium decreases, and finally disappears from the culture medium. For this reason, it is necessary to stop the culture when the 3-hydroxybutyric acid or the salt thereof is present in the culture medium.

The method of confirming the presence of 3-hydroxybutyric acid or salt thereof in the culture medium, which may vary depending on the type of strain, medium components, culture conditions, and other factors, is suitably determined in consideration of these factors. For example, the time to stop the culture can be determined while performing the culture using an analytical method, such as capillary electrophoresis.

Alternatively, since 3-hydroxybutyric acid is an acidic compound, the presence of 3-hydroxybutyric acid can be confirmed on the basis of decreases in pH of the medium during culture.

The salt of 3-hydroxybutyric acid is collected as alkali metal salt reacted with cations of alkali metal or alkaline earth metal, such as sodium or calcium, based on the inorganic salt contained in the culture medium. Accordingly, 3-hydroxybutyric acid can be produced by treating the collected culture medium by distillation or another common method. The collected culture medium may instead be subjected to purification by column chromatography using an appropriate column. Alternatively, the pH of the collected culture medium may be suitably changed, and either the desired 3-hydroxybutyric acid or salt thereof may be subjected to purification.

The amount of 3-hydroxybutyric acid or salt thereof obtained by the production process of the present invention in the medium, without containing lysates derived from the bacterial cells, is generally about 3 g or more, preferably 10 g or more, more preferably 15.3 g or more, even more preferably about 17.2 g or more, and most preferably about 20 g or more, per liter of the medium.

The present invention is described in more detail below with reference to an Example. Needless to say, the present invention is not limited to the Example.

EXAMPLE

Measurement of 3-Hydroxybutyric Acid or Salt Thereof

In order to measure the production of 3-hydroxybutyric acid or a salt thereof in a culture medium, the following experiment was performed by applying the technique of polyhydroxyalkanoate (PHA) analysis described in NPL 5.

After a culture medium obtained by the method described later was centrifuged, only the supernatant was taken, and 50 μL of the supernatant was dried. Methanol (0.50 ml) containing 3 vol % $H_2SO_4$ was added to the dried supernatant, and the mixture was heated at 105° C. for 1 hour to completely convert 3-hydroxybutyric acid or a salt thereof to methyl 3-hydroxybutyrate. After the mixture was cooled to room temperature, 0.50 ml of chloroform and 0.25 ml of distilled water were added, and the mixture was vigorously stirred. After centrifugation for one minute, 1 μl of chloroform layer was taken and analyzed for 3-hydroxybutyric acid using a gas chromatography apparatus. A preparation of 3-hydroxybutyric acid was treated and analyzed in the same manner as for the dried supernatant. Based on the preparation, the 3-hydroxybutyric acid accumulation rate per medium (3-hydroxybutyric acid (g)/supernatant liquid (L)) was calculated. The measured value by using an "F-kit D-3-hydroxybutyric acid" kit (J. K. International Inc.), which detects only D-isomer, matched the value measured by using the gas chromatography apparatus. This confirmed that almost all of the secreted 3-hydroxybutyric acid was D-isomer.

Measurement of PHB Accumulation Rate

In order to measure the amount of PHB accumulated in the cells, the following experiment was performed using the technique described in NPL 2.

The culture medium obtained above was centrifuged to obtain the bacterial cells alone, and the cells were washed with distilled water several times and then dried. Methanol (0.5 ml) containing 3 vol % $H_2SO_4$ was added to 1 to 3 mg of the dry cells, and heated at 105° C. for 3 hours. After the mixture was cooled to room temperature, 0.50 ml of chloroform and 0.25 ml of distilled water were added and vigorously stirred. After centrifugation for one minute, 1 μl of chloroform layer was taken and analyzed for PHAs using a gas chromatography apparatus. A preparation of PHB was treated and analyzed in the same manner as for the dry cells. Based on the preparation, the PHB accumulation rate per dry cell (PHB (g)/dry cell weight (g)) was calculated.

Example 1

In this Example, a process for producing 3-hydroxybutyric acid or a salt thereof using halophilic bacteria belonging to the genus *Halomonas* is described in detail.

A medium based on the modified SOT 5 (modified *Spirulina platensis* medium 5) shown in Table 1 was used. This medium was a *Spirulina platensis* medium (website of the National Institute for Environmental Studies), in which the amounts of $NaHCO_3$ and $Na_2CO_3$ were adjusted, the amount of $NaNO_3$ as a nitrogen source was increased by 5 times, and the amount of $K_2HPO_4$ as a phosphorus source was increased by 4 times. The pH of the medium after adjustment was 9.4±0.1. The medium was used as it is, without sterilization by using an autoclave, etc.

Various organic carbon sources were suitably added to the above medium during culture. The specific organic carbon source used was glycerin with a final concentration in the medium of 10% or 15%, or glucose with a final concentration of 10%.

TABLE 1

| Modified SOT 5 (modified *Spirulina platensis* medium) | | | |
|---|---|---|---|
| $NaHNO_3$ | 1.26 g | $Na_2CO_3$ | 0.53 g |
| $K_2HPO_4$ | 200 mg | $NaNO_3$ | 1250 mg |
| $K_2SO_4$ | 100 mg | NaCl | 100 mg |
| $MgSO_4 \cdot 7H_2O$ | 20 mg | $CaCl_2 \cdot 2H_2O$ | 4 mg |
| $FeSO_4 \cdot 7H_2O$ | 1 mg | $Na_2EDTA$ | 8 mg |
| A5 + Co solution | 0.1 ml | Distilled water | 100 ml |
| A5 + Co solution | | | |
| $H_3BO_3$ | 286 mg | $MnSO_4 \cdot 7H_2O$ | 250 mg |
| $ZnSO_4 \cdot 7H_2O$ | 22.2 mg | $CuSO_4 \cdot 5H_2O$ | 7.9 mg |
| $Na_2NoO_4 \cdot 2H_2O$ | 2.1 mg | $Co(NO_3) \cdot 6H_2O$ | 4.398 mg |
| Distilled water | 100 ml | | |

Pre-Culture of Halophilic Bacteria Belonging to Genus *Halomonas*

After plate culture of halophilic bacteria belonging to the genus *Halomonas* (*Halomonas* sp. KM-1 strain, *Halomonas*

*pantelleriensis* [ATCC 700273], and *Halomonas campisalis* [ATCC 700597]), 5 ml of the modified SOT 5 medium (containing 1 w/v % glucose, etc., as carbon sources in this case) above was placed in a test tube (diameter: 16.5 mm), and culture with shaking at 37° C. was carried out overnight.
Culture of Halophilic Bacteria Belonging to Genus *Halomonas*, Collection of Samples, etc.

The pre-cultured bacterial cells belonging to the genus *Halomonas* (0.2 ml) were seeded in 20 ml of the modified SOT 5 medium placed in a 100-ml Erlenmeyer flask, and the flask was closed with Silicosen. Culture with shaking was carried out at 33° C. at a stirring rate of 200 rpm. After 24 hours, 0.5 ml of culture medium was collected at intervals of about 12 hours, and the OD600, dry cell weight, PHB content, and the amount of 3-hydroxybutyric acid or salt thereof in the supernatant were measured.

As an organic carbon source, 5% of the organic carbon source was added to the medium at the beginning of growth, and 5% of the organic carbon source was further supplied at 24 hours after culture. When glucose or glycerol was used at a total of 15%, 5% of the organic carbon source was added to the medium at the beginning of growth, and 5% of the organic carbon source was further supplied at 24 hours and 36 hours after culture.

At the beginning of the culture, the cells were cultured under aerobic conditions at a stirring rate of 200 rpm. At the 36th hour, the conditions were changed to microaerobic conditions at a stirring rate of 50 rpm. After sampling the culture medium, the flask was again closed with Silicosen, and culture with shaking at 33° C. was continued for batch culture.

Figure 1:
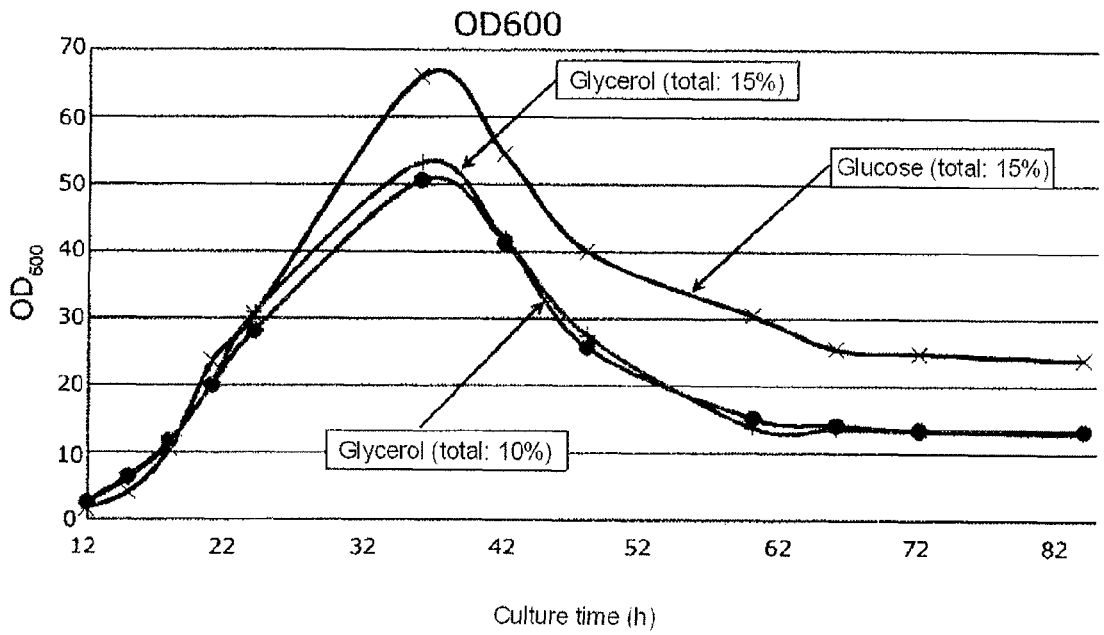
FIG. 1 is a graph showing the culture turbidity OD600 (vertical axis) and the culture time (horizontal axis: h) when halophilic bacterium *Halomonas* sp. KM-1 strain was cultured at 33° C. using glucose or glycerol. The symbol "%" shown in the legend represents "w/v %" (the same applies to FIGS. 2 to 7). When glycerol was used at a total of 10%, 5% of the carbon source was supplied at the beginning of growth and at 24 hours after culture. When glucose or glycerol was used at a total of 15%, 5% of the carbon source was supplied at the beginning of growth, and at 24 hours and 36 hours after culture. At the beginning of culture, the strain was cultured under aerobic conditions at 200 rpm. At the 36th hour, the conditions were changed to microaerobic conditions at 50 rpm. The following conditions are such that analytical values when the same culture was performed are shown in graphs.

FIGS. 1 and 2 show the status of growth of the *Halomonas* sp. KM-1 strain cultured at 33° C. using glucose or glycerol as a carbon source. FIGS. 3 and 4 show the yield of PHB when the *Halomonas* sp. KM-1 strain was cultured under the same conditions. FIG. 5 shows the yield of 3-hydroxybutyric acid or a salt thereof in the culture supernatant when the *Halomonas* sp. KM-1 strain was cultured under the same conditions.

When a medium containing glucose or glycerol as an organic carbon source at an initial concentration of 5% was used, and 5% of the organic carbon source was further added at the 24th hour and/or the 36th hour, no significant growth inhibition by the carbon source was observed. Generally, glucose, rather than glycerol, results in a faster growth speed and higher PHB accumulation. At the 36th hour, at which the air supply conditions were changed from aerobic conditions to microaerobic condition, 15% glucose led to a PHB accumulation of 32.5 g/L, and 10% glycerol and 15% glycerol led to a PHB accumulation of 21.5 g/L.

When the organic carbon source was 15% glucose, 81% of PHB was degraded, and 20 g of 3-hydroxybutyric acid or salt thereof was secreted into the medium.

When the organic carbon source was 10% glycerol or 15% glycerol, almost 100% of PHB was degraded in either case, and 15.3 g and 17.2 g of 3-hydroxybutyric acid or salt thereof were secreted into the medium, respectively.

The above results revealed that when a medium containing glucose, glycerol, or the like as an organic carbon source was used, the *Halomonas* sp. KM-1 strain could produce 3-hydroxybutyric acid or a salt thereof with a yield of 15.3 g or more per liter of the medium. This suggested the possibility that when the amount of PHB accumulation increased, particularly in the case of glycerol, most of the accumulated PHB was degraded and secreted into the medium as 3-hydroxybutyric acid or a salt thereof.

FIGS. 6 and 7 show the status of growth of the halophilic bacteria, i.e., *Halomonas* sp. KM-1 strain, *Halomonas pantelleriensis* (ATCC 700273), and *Halomonas campisalis* (ATCC 700597), cultured at 33° C. using 10% glycerol. FIGS. 8 and 9 show the yield of PHB when the halophilic bacteria were cultured under the same conditions. FIG. 10 shows the yield of 3-hydroxybutyric acid or a salt thereof in the supernatant of the culture medium when the halophilic bacteria were cultured under the same conditions.

When 10% glycerol was used as a carbon source, the halophilic bacteria, i.e., *Halomonas* sp. KM-1 strain, *Halomonas pantelleriensis*, and *Halomonas campisalis*, grew in different ways. At the 48th hour, at which the air supply conditions were changed from aerobic conditions to microaerobic conditions, the halophilic bacteria, i.e., *Halomonas* sp. KM-1 strain, *Halomonas pantelleriensis*, and *Halomonas campisalis*, accumulated PHB in respective amounts of 16.0 g/L, 5.8 g/L, and 7.3 g/L. Moreover, the halophilic bacteria, *Halomonas* sp. KM-1 strain, *Halomonas pantelleriensis*, and *Halomonas campisalis*, led to 98%, 46%, and 41% of PHB degradation, respectively, and resulted in the production of 3-hydroxybutyric acid in the medium in respective amounts of 16 g, 2.6 g, and 3.0 g.

The above results revealed that when a medium containing glucose, glycerol, or the like as an organic carbon source was used, the *Halomonas* sp. KM-1 strain could produce 3-hydroxybutyric acid with a yield of 14 g or more per liter of the medium. This suggested the possibility that when the amount of PHB accumulation was increased, particularly in the case of glycerol, most of the accumulated PHB was degraded and mostly produced as 3-hydroxybutyric acid in the culture medium.

The concentration of the nitrogen source during culture within a certain range causes no difference in PHB accumulation, as shown in PTL 3 and PTL 5.

Furthermore, other halophilic bacteria belonging to the genus *Halomonas* showed the same tendency, as shown in FIGS. 6, 7, 8, 9, and 10.

The dissolved oxygen amount of the medium was measured with a Horiba D-55 dissolved oxygen meter. The dissolved oxygen amounts at 200 rpm and 50 rpm were 0.2 to 0.4 mg/ml and 0.11 to 0.21 mg/ml, respectively.

It was also revealed that the amount of DNA in the medium when the *Halomonas* sp. KM-1 strain was cultured under microaerobic conditions for 72 hours was 2.31 mg/L, which was greater than the DNA amount (0.25 mg/L) in the culture under aerobic conditions, but was kept down to about 0.6% of the DNA amount (384 mg/L) in the culture under anaerobic conditions.

The amount of DNA in the culture medium when the strain was cultured under microaerobic conditions for 72 hours did not exceed the above value (2.31 mg/L).

Sequence Listing

---

The invention claimed is:

1. A process for producing 3-hydroxybutyric acid or a salt thereof, the process comprising the following steps (1) to (3):
   (1) step 1 of culturing one or more halophilic bacteria belonging to the genus *Halomonas* under aerobic conditions in a medium containing an inorganic salt and one or more organic carbon sources;
   (2) step 2 of changing the culture conditions in step 1 from aerobic culture to microaerobic culture, and culturing bacterial cells of the halophilic bacteria to produce 3-hydroxybutyric acid or a salt thereof that is secreted from the bacterial cells into a culture medium; and
   (3) step 3 of collecting the 3-hydroxybutyric acid or the salt thereof from the culture medium obtained in step 2.

2. The process according to claim 1, wherein the 3-hydroxybutyric acid or the salt thereof is contained in an amount of 3 g or more per liter of the culture medium obtained in step 2.

3. The process according to claim 2, wherein the organic carbon sources comprise glycerol or waste glycerol.

4. The process according to claim 3, wherein the halophilic bacteria comprise *Halomonas* sp. KM-1 strain (FERM BP-10995).

5. The process according to claim 2, wherein the halophilic bacteria comprise *Halomonas* sp. KM-1 strain (FERM BP-10995).

6. The process according to claim 1, wherein the organic carbon sources comprise glycerol or waste glycerol.

7. The process according to claim 6, wherein the halophilic bacteria comprise *Halomonas* sp. KM-1 strain (FERM BP-10995).

8. The process according to claim 1, wherein the halophilic bacteria comprise *Halomonas* sp. KM-1 strain (FERM BP-10995).

* * * * *